(12) United States Patent
Imai

(10) Patent No.: US 10,314,472 B2
(45) Date of Patent: Jun. 11, 2019

(54) MEDICAL DILATOR

(71) Applicant: OLYMPUS CORPORATION, Hachioji-shi, Tokyo (JP)

(72) Inventor: Shigeru Imai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 176 days.

(21) Appl. No.: 15/218,298

(22) Filed: Jul. 25, 2016

(65) Prior Publication Data

US 2016/0331223 A1 Nov. 17, 2016

Related U.S. Application Data

(63) Continuation of application No. PCT/JP2015/063337, filed on May 8, 2015.

(30) Foreign Application Priority Data

Jul. 23, 2014 (JP) ................................. 2014-150052

(51) Int. Cl.

| A61B 1/32 | (2006.01) |
|---|---|
| A61B 17/24 | (2006.01) |
| A61B 90/50 | (2016.01) |
| A61B 17/02 | (2006.01) |
| A61B 1/24 | (2006.01) |

(52) U.S. Cl.
CPC ................ *A61B 1/32* (2013.01); *A61B 1/24* (2013.01); *A61B 17/0206* (2013.01); *A61B 17/0293* (2013.01); *A61B 90/50* (2016.02); *A61B 17/24* (2013.01)

(58) Field of Classification Search
CPC .. A61B 1/24; A61B 1/32; A61B 17/02; A61B 17/0206; A61B 17/0293; A61B 17/24; A61B 90/50
See application file for complete search history.

(56) References Cited

U.S. PATENT DOCUMENTS

2014/0031632 A1* 1/2014 Nakao ................ A61B 17/0206
600/206

FOREIGN PATENT DOCUMENTS

| FR | 381393 A * | 1/1908 | ............... A61B 1/24 |
|---|---|---|---|
| JP | 2000-507146 A | 6/2000 | |
| JP | 2002-153476 A | 5/2002 | |
| JP | 2012-254212 A | 12/2012 | |

OTHER PUBLICATIONS

Jul. 21, 2015 International Search Report issued in Patent Application No. PCT/JP2015/063337.
Feb. 2, 2017 Transmittal of Translation of International Preliminary Report on Patentability issued in International Patent Application No. PCT/JP2015/063337.

* cited by examiner

*Primary Examiner* — Christian A Sevilla
(74) *Attorney, Agent, or Firm* — Oliff PLC

(57) ABSTRACT

A medical dilator includes a keeper section and an auxiliary member. The auxiliary member includes an insertion section configured to be insertable in an opening part, and a support section which is disposed on the insertion section, thereby being inserted in the opening part together with the insertion section, and disposed to cross a direction of insertion of a treatment instrument into the opening part, the support section being configured to support the treatment instrument which is inserted in the opening part.

6 Claims, 10 Drawing Sheets

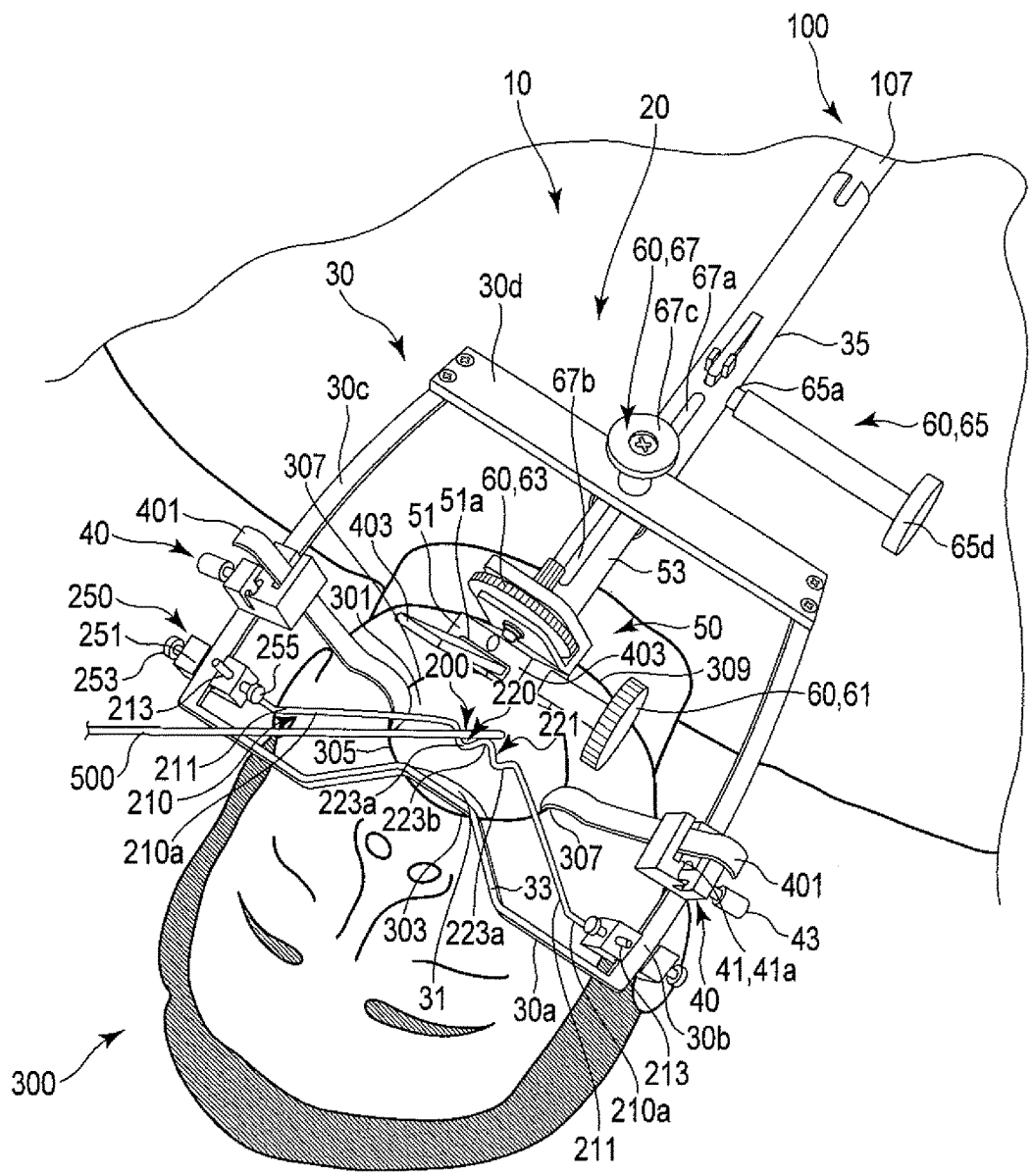
F I G. 1A

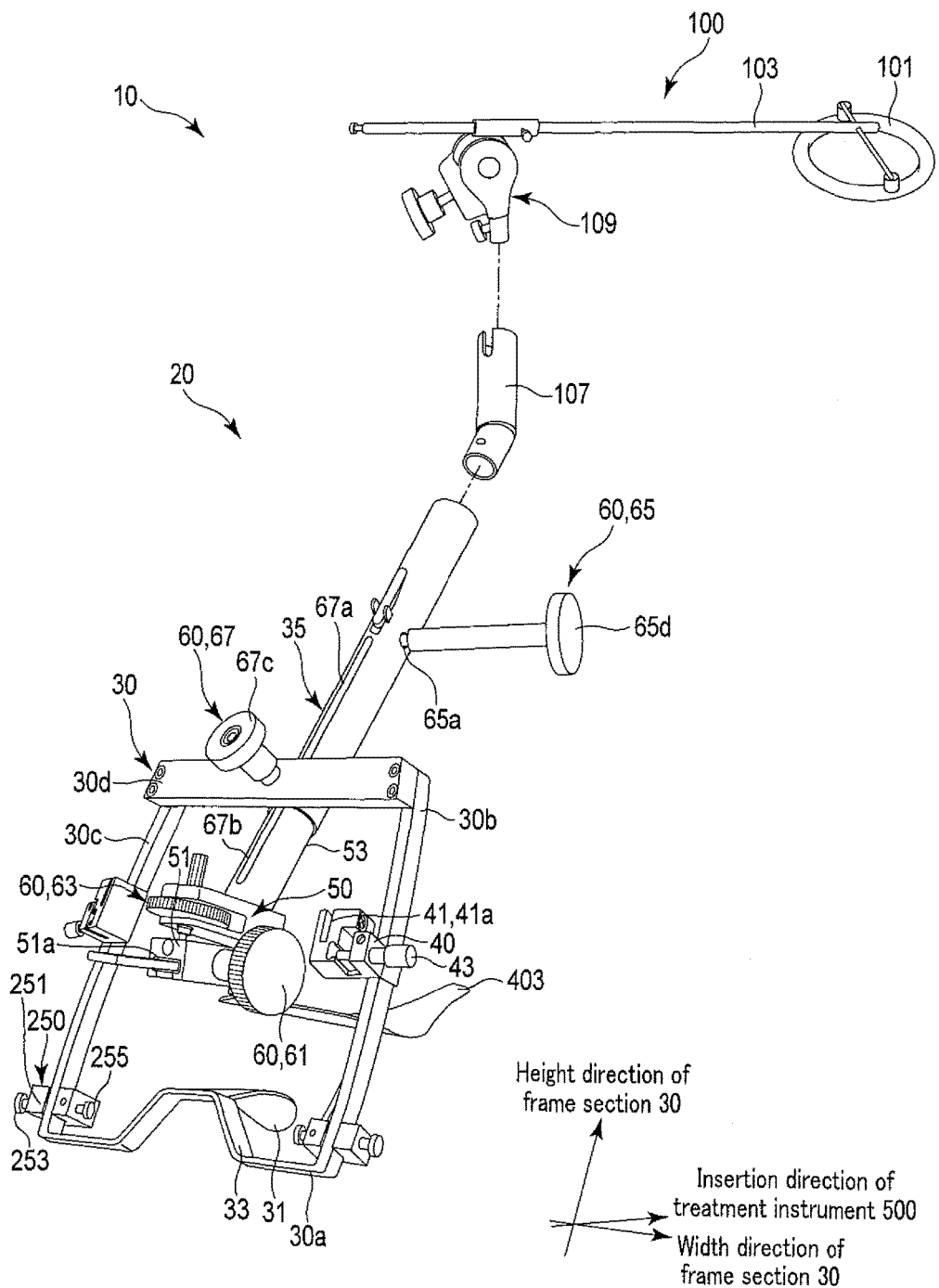
F I G. 1D

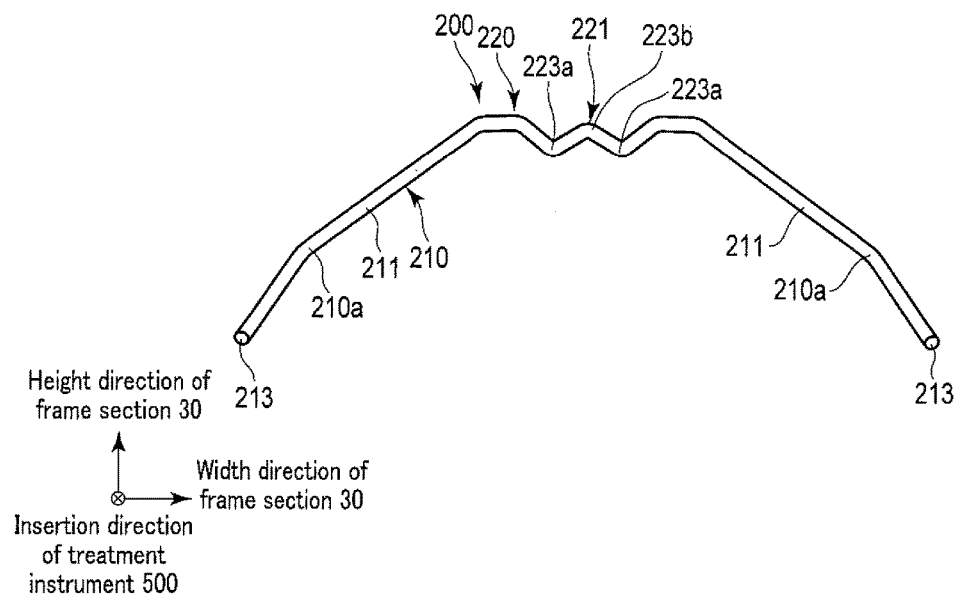
F I G. 2A
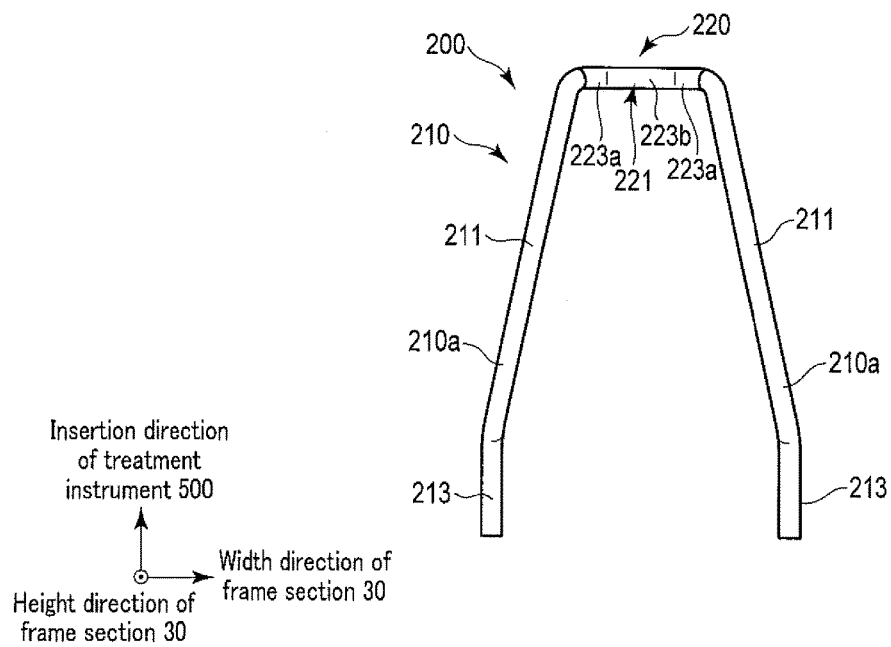
F I G. 2B

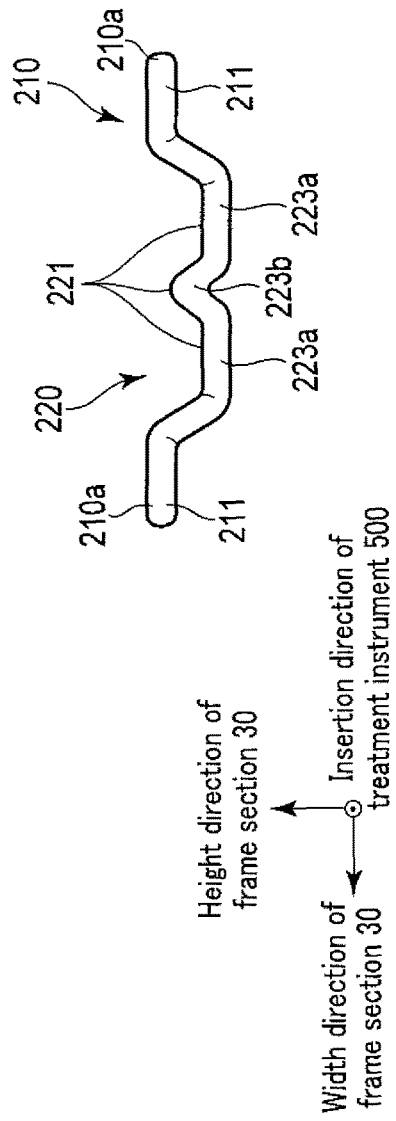
F I G. 2E
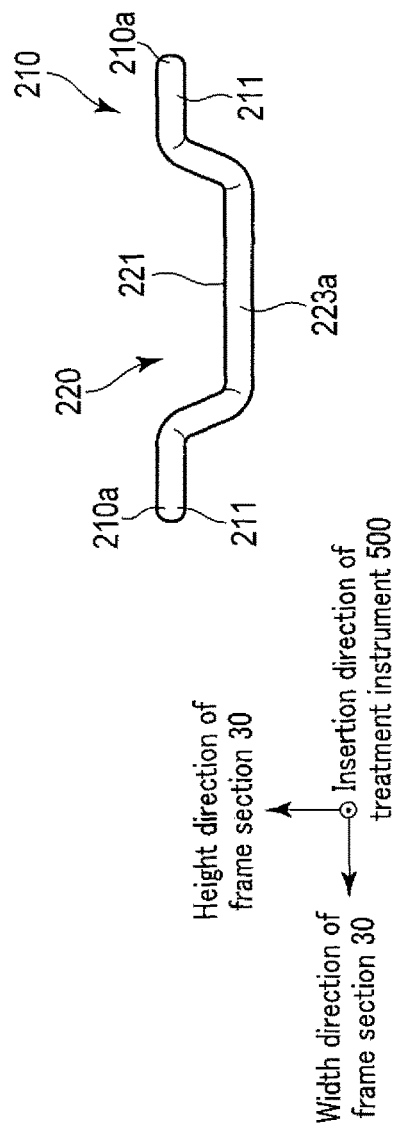
F I G. 2F

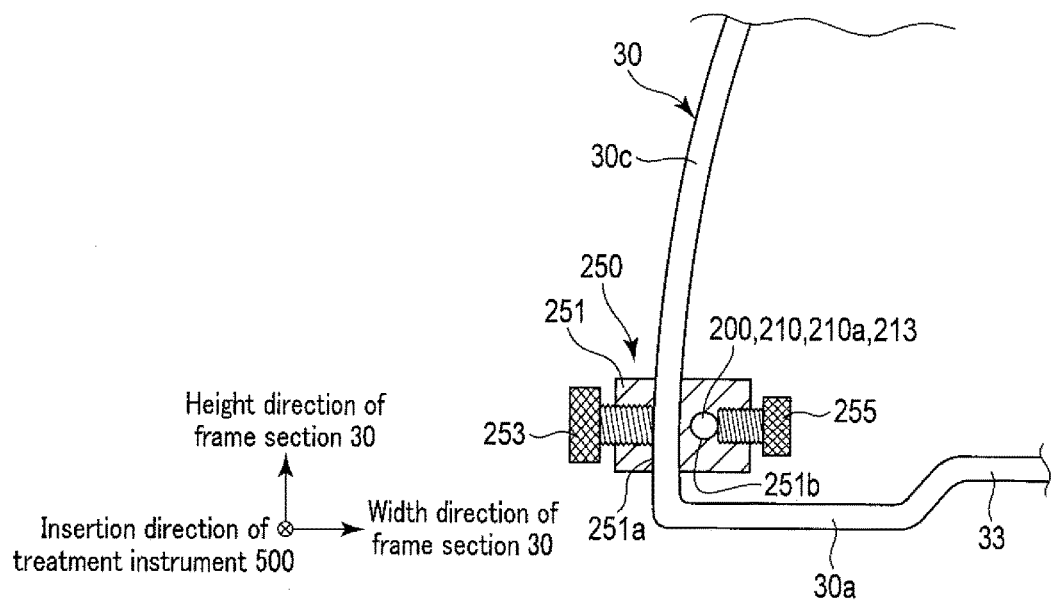
F I G. 3A
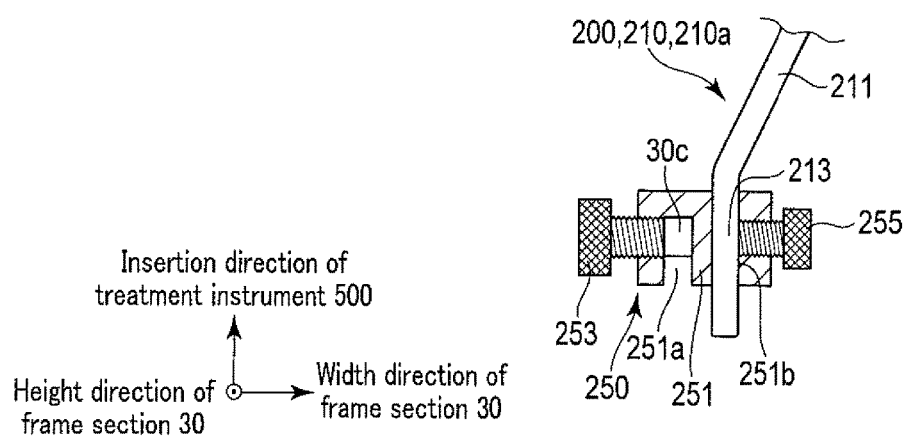
F I G. 3B

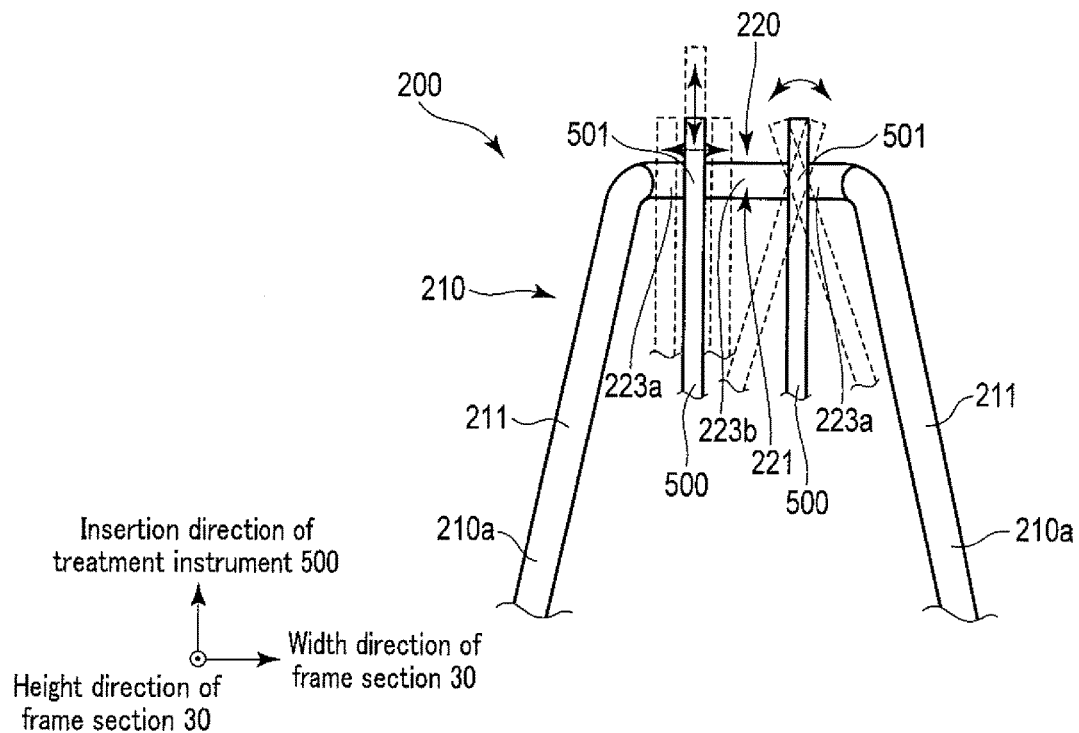
F I G. 4A
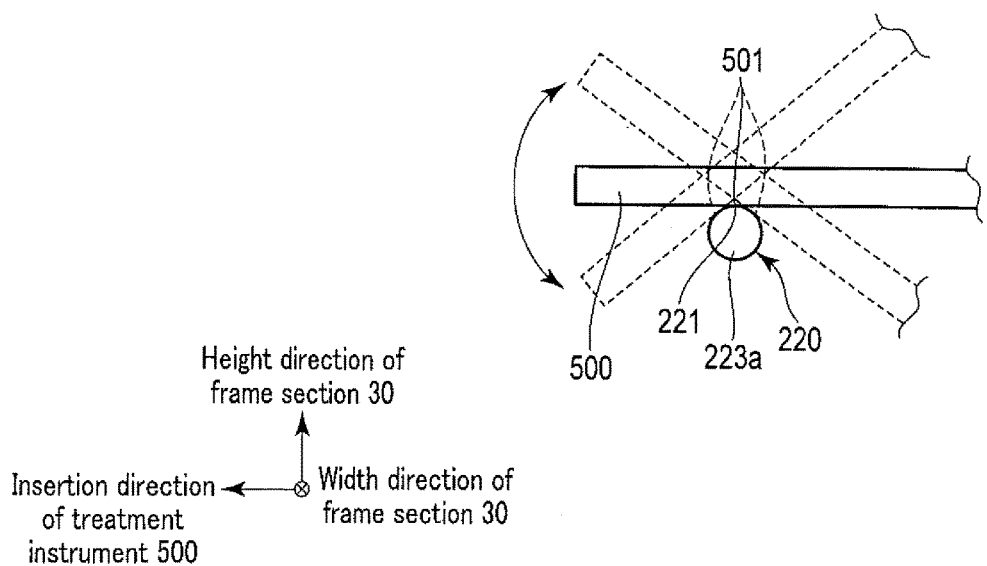
F I G. 4B

MEDICAL DILATOR

CROSS-REFERENCE TO RELATED APPLICATIONS

This application is a Continuation application of PCT Application No. PCT/JP2015/063337, filed May 8, 2015 and based upon and claiming the benefit of priority from prior Japanese Patent Application No. 2014-150052, filed Jul. 23, 2014, the entire contents of all of which are incorporated herein by reference.

BACKGROUND OF THE INVENTION

1. Field of the Invention

The present invention relates to a medical dilator which dilates an opening part such as the oral cavity.

2. Description of the Related Art

In general, in a peroral larynx microsurgery which is performed on, for example, the vocal cords, used is made of a frame-shaped medical dilator which dilates the oral cavity that is an opening part, and keeps the dilated state of the oral cavity. When the medical dilator dilates the oral cavity and keeps the dilated state, a surgeon inserts, for example, an insertion section provided at a distal end portion of an endoscope, which is suspended, from the oral cavity into a lumen. Then, the surgeon views an affected part which is displayed on a display unit which is disposed at a proximal end portion of the endoscope and is exposed on an outside of the oral cavity. For example, in the state in which the surgeon is viewing the affected part, the surgeon holds a proximal end portion of one treatment instrument by the right hand, and holds a proximal end portion of the other treatment instrument by the left hand. Then, in the state in which a distal end portion of the one treatment instrument, the insertion section, and a distal end portion of the other treatment instrument are arranged, for example, in the named order from a right side of the oral cavity to a left side of the oral cavity, the surgeon inserts the distal end portions of these treatment instruments, from both the left and right sides of the insertion section, into the lumen via the oral cavity. The surgeon treats, by the treatment instruments, vocal cords in a larynx that is the lumen continuous with the oral cavity. Such treatment instruments include, for instance, grasping forceps and an electric scalpel.

In Jpn. Pat. Appln. KOKAI Publication No. 2012-254212, for example, such a medical dilator is disclosed as an oral cavity dilator which keeps the oral cavity in the dilated state.

BRIEF SUMMARY OF THE INVENTION

An aspect of a medical dilator of the present invention includes a keeper section inserted in an opening part of a subject, and configured to dilate the opening part and to keep a dilated state of the opening part; and an auxiliary member disposed in the keeper section, and configured to assist a treatment operation of a treatment instrument which is configured to treat the opening part and a lumen communicating with the opening part, wherein the auxiliary member includes: an insertion section configured to be insertable in the opening part; and a support section which is disposed on the insertion section, thereby being inserted in the opening part together with the insertion section, and disposed to cross a direction of insertion of the treatment instrument into the opening part, the support section being configured to support the treatment instrument which is inserted in the opening part.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a perspective view of the vicinity of a keeper section at a time when a medical dilator according to an embodiment of the present invention was attached to a patient.

FIG. 1D is a perspective view of the medical dilator in a state in which a first dilation-keeping member, a second dilation-keeping member and the auxiliary member are removed.

FIG. 2A is a perspective view of the auxiliary member.

FIG. 2B is a top view of the auxiliary member.

FIG. 2E illustrates an example of the support section, FIG. 2E being is a front view of the support section.

FIG. 2F illustrates an example of the support section, FIG. 2F being is a front view of the support section.

FIG. 3A is a view illustrating the configuration of a positioning/fixing member.

FIG. 3B is a view illustrating the configuration of the positioning/fixing member.

FIG. 4A is a view illustrating the inclining of a treatment instrument relative to a support surface about a fulcrum in a state in which the treatment instrument is supported on the support surface, and, more specifically, FIG. 4A is a view illustrating the rotation of the treatment instrument about the fulcrum in a direction about a height direction of a frame section, and is a view illustrating the sliding of the treatment instrument on the support surface in the axial direction of the treatment instrument and in the width direction of the frame section in the state in which the treatment instrument is supported on the support surface.

FIG. 4B is a view illustrating the inclining of the treatment instrument relative to the support surface about the fulcrum in the state in which the treatment instrument is supported on the support surface, FIG. 4B being a view illustrating the rotation of the treatment instrument about the fulcrum in a direction about the width direction of the frame section.

DETAILED DESCRIPTION OF THE INVENTION

Embodiments of the present invention will be described hereinafter in detail with reference to the accompanying drawings.

[One Embodiment]
[Configuration]

An embodiment will be described with reference to FIG. 1A, FIG. 1B, FIG. 1C, FIG. 1D, FIG. 2A, FIG. 2B, FIG. 2C, FIG. 2D, FIG. 2E, FIG. 2F, FIG. 3A, FIG. 3B, FIG. 4A, and FIG. 4B. In some drawings, depiction of some of members is omitted for the purpose of clearer illustration.

[Medical Dilator 10]

As illustrated in FIG. 1A, a medical dilator 10 includes a keeper section 20 which is inserted in an opening part 301 of a subject 300, dilates the opening part 301, and keeps a dilated state of the opening part. The opening part 301, in which the keeper section 20 is inserted, is, for instance, the oral cavity, and is openable/closable.

Figure 1B:
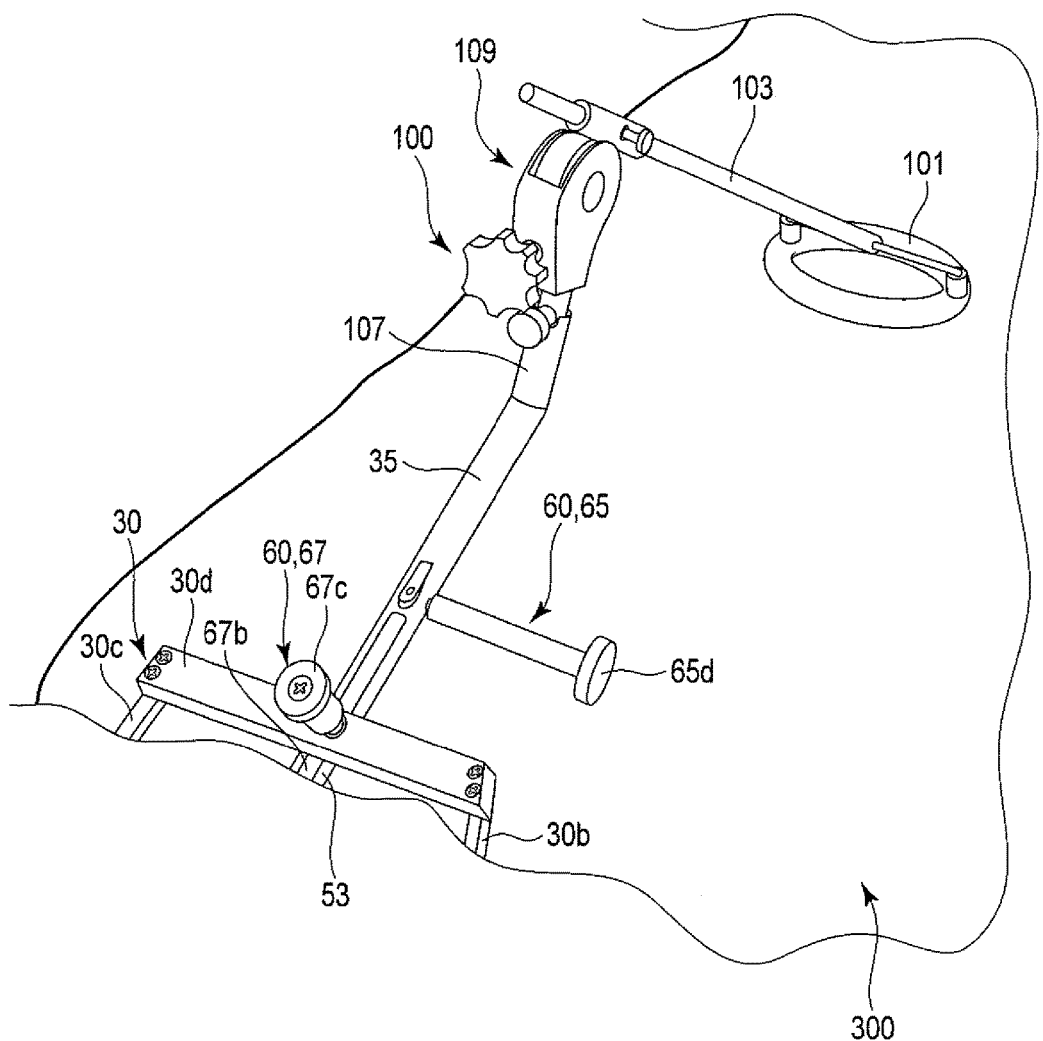
FIG. 1B is a perspective view of the vicinity of a support unit at a time when the medical dilator was attached to the patient.

As illustrated in FIG. 1B, the medical dilator 10 further includes a support unit 100 which supports the keeper section 20 in a state in which the keeper section 20 is positioned and fixed relative to the subject 300.

[Keeper Section 20]

Figure 1C:
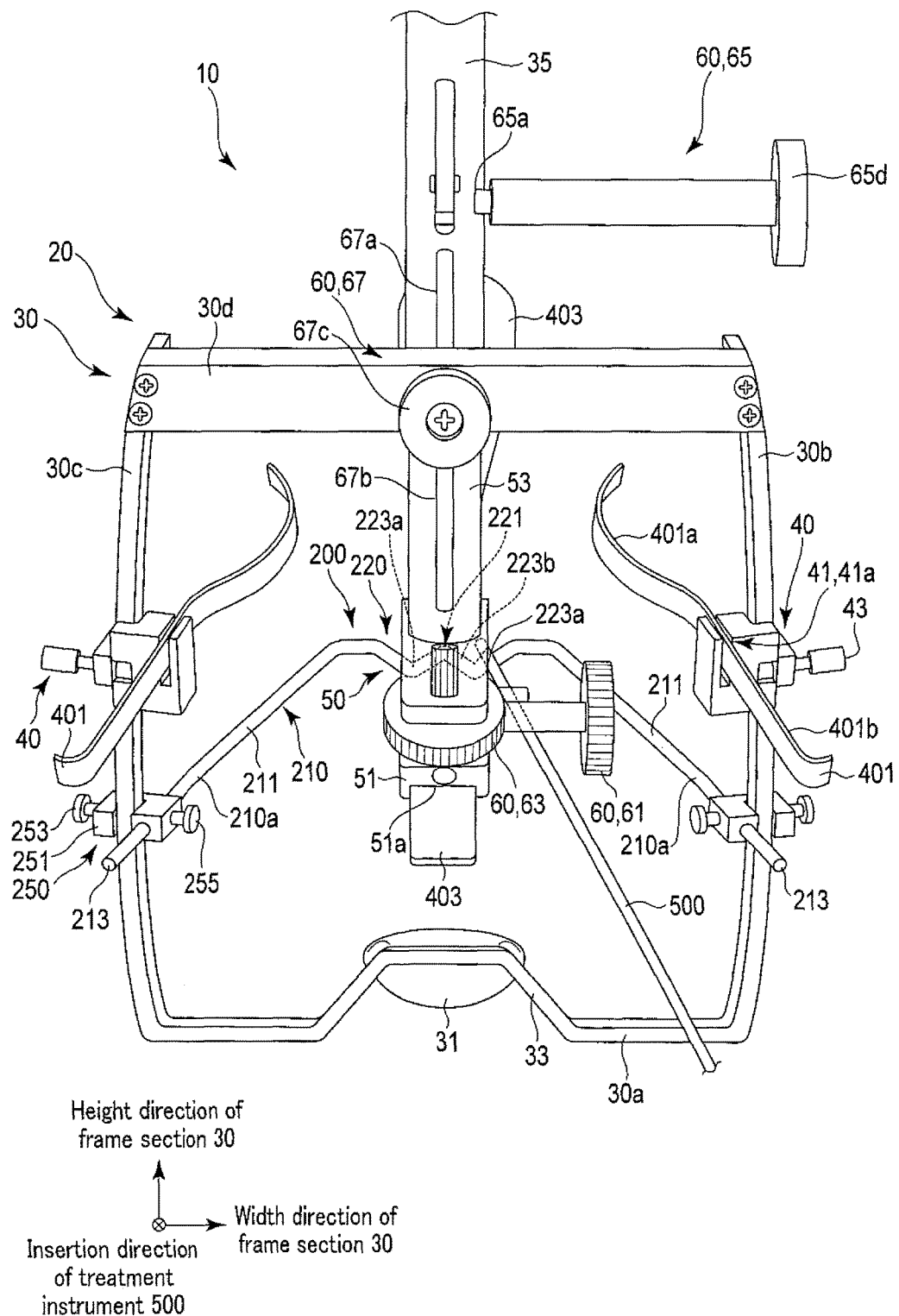
FIG. 1C is a front view of the keeper section including an auxiliary member.

As illustrated in FIG. 1A, FIG. 1C and FIG. 1D, the keeper section 20 includes a rectangular frame section 30 including, for example, a lower side portion 30a, a right side portion 30b, a left side portion 30c and an upper side portion 30d; and a pair of positioning/fixing sections 40 which are disposed on the right side portion 30b and left side portion 30c in a state in which the positioning/fixing sections 40 are movable in the height direction of the frame section 30. The keeper section 20 further includes a holding unit 50 which is disposed on the upper side portion 30d in a manner to be movable in the height direction of the frame section 30, and an adjusting unit 60. This keeper section 20 is formed of, for example, a metal.

[Frame Section 30]

As illustrated in FIG. 1A, FIG. 1C and FIG. 1D, in the frame section 30, the right side portion 30b and left side portion 30c are disposed along the height direction of the frame section 30, and the lower side portion 30a and upper side portion 30d are disposed along the width direction of the frame section 30, which is perpendicular to the height direction. The right side portion 30b is opposed to the left side portion 30c in the width direction of the frame section 30. The lower side portion 30a is opposed to the upper side portion 30d in the height direction of the frame section 30.

One end portion of of the right side portion 30b is continuous with one end portion of the lower side portion 30a, and one end portion of the left side portion 30c is continuous with the other end portion of the lower side portion 30a. In this manner, the lower side portion 30a, right side portion 30b and left side portion 30c are formed as an integral body.

One end portion of the upper side portion 30d is coupled to the other end portion of the right side portion 30b, for example, by screws. The other end portion of the upper side portion 30d is coupled to the other end portion of the left side portion 30c, for example, by screws.

As illustrated in FIG. 1A, the lower side portion 30a is disposed on the side of the upper row 303 of teeth and on the side of the upper jaw 305 of the subject 300 (patient). The right side portion 30b and left side portion 30c are disposed on the sides of the angles of mouth 307. The upper side portion 30d is disposed on the side of the lower jaw 309.

As illustrated in FIG. 1A, FIG. 1C and FIG. 1D, the frame section 30 includes a protection portion 31 which is provided on the lower side portion 30a, and protects the upper row 303 of teeth by being inserted in the opening part 301 and covering the upper row 303 of teeth. The protection portion 31 functions as a protector. The protection portion 31 is integral with the lower side portion 30a. For example, the protection portion 31 is disposed at a central part of the lower side portion 30a. The protection portion 31 is disposed along an insertion direction of a treatment instrument 500 (to be described later), which is perpendicular to the height direction of the frame section 30 and the width direction of the frame section 30, and the protection portion 31 is inserted in the opening part 301.

As illustrated in FIG. 1A, FIG. 1C and FIG. 1D, the frame section 30 includes an upper jaw fixation portion 33 which is mounted on the upper jaw 305 and fixed to the upper jaw 305. The upper jaw fixation portion 33 is formed by projecting (bending) a part of the lower side portion 30a toward the upper side portion 30d. The upper jaw fixation portion 33 is disposed in the vicinity of that part of the lower side portion 30a, at which the protection portion 31 is disposed. The upper jaw fixation portion 33 is integral with the protection portion 31.

As illustrated in FIG. 1A, FIG. 1B, FIG. 1C and FIG. 1D, the frame section 30 includes a cylindrical portion 35 which is provided along the height direction of the frame portion 30 and is disposed at a middle part of the upper side portion 30d. The cylindrical portion 35 includes a distal end portion which is open to the lower side portion 30a in the height direction of the frame section 30 and is formed integral with the upper side portion 30d; and a proximal end portion which is open in a direction opposite to the distal end portion along the height direction of the frame section 30 and is provided to extend to an outside to the frame section 30.

[Positioning/Fixing Section 40]

As illustrated in FIG. 1A, FIG. 1C and FIG. 1D, the positioning/fixing section 40 positions and fixes a first dilation-keeping member 401 relative to the frame section 30. As illustrated in FIG. 1A, the first dilation-keeping member 401 is inserted in the opening part 301, dilates the angle of mouth 307, and keeps the dilated state. As illustrated in FIG. 1C, for example, the first dilation-keeping member 401 is a metallic elongated plate-shaped member. A distal end portion of the first dilation-keeping member 401 is recessed from the right side portion 30b toward the center of the frame section 30, and is formed in a curved shape. Thereby, a recess portion 401a is formed. The bottom surface of the recess portion 401a is provided on the center side of the frame section 30, relative to the planar surface of a proximal end portion 401b of the first dilation-keeping member 401. This first dilation-keeping member 401 functions as a retractor. The first dilation-keeping member 401 is replaceable in relation to the medical dilator 10, in accordance with the treatment instrument 500 to be used, a therapy technique, the position of an affected part, and the subject 300.

As illustrated in FIG. 1A, FIG. 1C and FIG. 1D, the positioning/fixing section 40 includes a first insertion amount adjusting portion 41 which adjusts the insertion amount of the first dilation-keeping member 401 into the opening part 301. The first insertion amount adjusting portion 41 includes a groove portion 41a which is disposed on the inside of the frame section 30, and in which the first dilation-keeping member 401 is detachably fitted. The first dilation-keeping member 401 is attached to the positioning/fixing section 40, by the first dilation-keeping member 401 being fitted in the groove portion 41a. In this manner, the first dilation-keeping member 401 can be replaced with some other first dilation-keeping member 401.

In the axial direction of the first dilation-keeping member 401, the position of attachment of the first dilation-keeping member 401 to the groove portion 41a is desirably determined in advance in accordance with each individual first dilation-keeping member 401. In this manner, the amount of insertion of the first dilation-keeping member 401 into the opening part 301 is desirably set in accordance with the length of the first dilation-keeping member 401 itself, which is fitted in the groove portion 41a.

In the meantime, the position of attachment may be freely set in the axial direction of the first dilation-keeping member 401 in accordance with the treatment instrument 500 to be used, a therapy technique, the position of an affected part, and the subject 300. Thus, the amount of insertion of the first dilation-keeping member 401 into the opening part 301 may desirably be set in accordance with the position of attachment of the first dilation-keeping member 401 to the groove portion 41a.

The positioning/fixing section 40 is disposed, for example, so as to be slidable on the right side portion 30b along the right side portion 30b in the height direction of the frame section 30. In addition, the positioning/fixing section 40 is positioned and fixed relative to the right side portion 30b, for example, by a screw 43. Thus, in the state in which the first dilation-keeping member 401 is fitted in the groove portion 41a, the positioning/fixing section 40 slides along the right side portion 30b, and the positioning/fixing section 40 is positioned and fixed relative to the right side portion 30b, for example, by the screw 43. Thereby, in the state in which the position of the first dilation-keeping member 401 at the right side portion 30b is adjusted in the height direction of the frame section 30, the positioning/fixing section 40 positions and fixes the first dilation-keeping member 401 relative to the right side portion 30b in the height direction of the frame section 30. By adjusting the position of the first dilation-keeping member 401 at the right side portion 30b, the positioning/fixing section 40 adjusts the position of the first dilation-keeping member 401 relative to the angle of mouth 307. Incidentally, the above applies similarly to the left side portion 30c.

The positioning/fixing section 40 is freely attachable/detachable to/from the right side portion 30b by the screw 43, and is replaceable with some other positioning/fixing section 40. Incidentally, the above applies similarly to the left side portion 30c.

[Holding Unit 50]

As illustrated in FIG. 1A, FIG. 1C and FIG. 1D, the holding unit 50 holds a second dilation-keeping member 403. The second dilation-keeping member 403 is inserted in the opening part 301, dilates the lower jaw 309 side of the opening part 301, and keeps the dilated state. A distal end portion of the second dilation-keeping member 403 comes in contact with, for example, the larynx, or the root of the tongue, or the hypopharynx and the upper part of the esophagus, in accordance with the treatment instrument 500 to be used, a therapy technique, the position of an affected part, and the subject 300. As illustrated in FIG. 1C and FIG. 1D, for example, the second dilation-keeping member 403 is a metallic elongated plate-shaped member. This second dilation-keeping member 403 functions as a spatula-shaped blade. The second dilation-keeping member 403 is replaceable in relation to the medical dilator 10 (holding unit 50), in accordance with the treatment instrument 500 to be used, a therapy technique, the position of an affected part, and the subject 300.

As illustrated in FIG. 1A, FIG. 1C and FIG. 1D, the holding unit 50 includes a holding portion 51 in/from which the second dilation-keeping member 403 can be inserted/removed and which holds the second dilation-keeping member 403 that is inserted in the holding portion 51; and a cylindrical suspension portion 53 which suspends the holding portion 51 relative to the upper side portion 30d.

As illustrated in FIG. 1A, FIG. 1C and FIG. 1D, the holding portion 51 holds a proximal end portion of the second dilation-keeping member 403, for example, such that a distal end portion of the second dilation-keeping member 403 can be inserted in the opening part 301 in the axial direction of the second dilation-keeping member 403. The holding portion 51 includes a groove portion 51a in/from which the second dilation-keeping member 403 can freely be inserted/removed. The groove portion 51a is disposed along the insertion direction of the treatment instrument 500, which is the axial direction of the holding portion 51. Since the second dilation-keeping member 403 can freely be inserted/removed in/from the holding portion 51, the second dilation-keeping member 403 is, as described above, replaceable in relation to the medical dilator 10 (holding unit 50), in accordance with the treatment instrument 500 to be used, the therapy technique, the position of the affected part, and the subject 300.

As illustrated in FIG. 1A, FIG. 1C and FIG. 1D, the suspension portion 53 includes a distal end portion which is coupled to the holding portion 51 and is disposed within the frame section 30, and a proximal end portion which is inserted/removed in/from the cylindrical portion 35. The suspension portion 53 is inserted in the cylindrical portion 35, and the axial direction of the suspension portion 53 extends along the height direction of the frame section 30. The suspension portion 53 is slidable relative to the cylindrical portion 35 in the axial direction of the suspension portion 53. In this case, the suspension portion 53 is formed as an inside cylinder portion, and the cylindrical portion 35 is formed as an outside cylinder portion.

[Adjusting Unit 60]

As illustrated in FIG. 1A, FIG. 1C and FIG. 1D, the adjusting unit 60 adjusts the amount of insertion of the second dilation-keeping member 403 into the opening part 301, the direction of insertion of the second dilation-keeping member 403 into the opening part 301, and the position of insertion of the second dilation-keeping member 403 into the opening part 301.

Thus, as illustrated in FIG. 1A, FIG. 1C and FIG. 1D, the adjusting unit 60 includes an adjustment-side fixing section 61 which is disposed on the holding portion 51 and fixes the second dilation-keeping member 403 to the holding portion 51 in the state in which the amount of insertion of the second dilation-keeping member 403 into the opening part 301 is adjusted. The adjusting unit 60 includes an insertion direction-adjusting section 63 which is disposed on one end portion of the suspension portion 53 and adjusts the direction of insertion of the second dilation-keeping member 403 into the opening part 301. The adjusting unit 60 includes a position-adjusting mechanism 65 which is disposed on the cylindrical portion 35 and suspension portion 53 and adjusts the position of insertion of the second dilation-keeping member 403 into the opening part 301. The adjusting unit 60 includes a position-fixing mechanism 67 which is disposed on the cylindrical portion 35, suspension portion 53 and upper side portion 30d, and fixes the insertion position of the second dilation-keeping member 403 which was adjusted by the position-adjusting mechanism 65.

[Adjustment-Side Fixing Section 61]

As illustrated in FIG. 1A, FIG. 1C and FIG. 1D, in the axial direction of the second dilation-keeping member 403, the position of attachment of the second dilation-keeping member 403 to the groove portion 51a is desirably determined in advance in accordance with each individual second dilation-keeping member 403. In this manner, the amount of insertion of the second dilation-keeping member 403 into the opening part 301 is desirably set in accordance with the length of the second dilation-keeping member 403 itself, which is inserted in the groove portion 51a. In this case, the adjustment-side fixing section 61 fixes a predetermined part of the proximal end portion of the second dilation-keeping member 403 to the holding portion 51, without the insertion amount being adjusted.

In the meantime, the position of attachment may freely be set in the axial direction of the second dilation-keeping member 403 in accordance with the treatment instrument 500 to be used, a therapy technique, the position of an affected part, and the subject 300. In this manner, in accordance with the attachment position of the second dilation-keeping member 403 to the groove portion 51a, the amount of insertion of the second dilation-keeping member 403 into the opening part 301 may desirably be set. In this case, the adjustment-side fixing section 61 fixes the proximal end portion of the second dilation-keeping member 403 to the holding portion 51, in the state in which the insertion amount of the second dilation-keeping member 403 was adjusted.

The adjustment-side fixing section 61 includes an adjusting screw which fixes the second dilation-keeping member 403, which is inserted in the groove portion 51a, to the holding portion 51.

[Insertion Direction-Adjusting Section 63]

The insertion direction-adjusting section 63, as illustrated in FIG. 1A, FIG. 1C and FIG. 1D, adjusts the direction and inclination of the holding portion 51 relative to the suspension portion 53, thereby adjusting the direction of insertion of the second dilation-keeping member 403 into the opening part 301, and fixing the insertion direction. The insertion direction-adjusting section 63 includes an adjusting screw which adjusts the direction and inclination of the holding portion 51 relative to the suspension portion 53.

[Position-Adjusting Mechanism 65]

The position-adjusting mechanism 65, as illustrated in FIG. 1A, FIG. 1C and FIG. 1D, includes a cylinder-side adjusting hole portion 65a which is provided in a peripheral surface of the cylindrical portion 35 along the thickness direction of the cylindrical portion 35; and a suspension-side adjustment length groove portion (not shown) which overlaps the cylinder-side adjusting hole portion 65a and is provided in a peripheral surface of the suspension portion 53 along the axial direction of the suspension portion 53. The cylinder-side adjusting hole portion 65a penetrates the cylindrical portion 35, and communicates with the suspension-side adjustment length groove portion. The position-adjusting mechanism 65 further includes a rack portion (not shown) including projection portions and recess portions provided on an inner peripheral surface of the suspension portion 53; and an adjusting member 65d which is inserted through the cylinder-side adjusting hole portion 65a and the suspension-side adjustment length groove portion, and is journaled in the cylindrical portion 35.

For example, the cylinder-side adjusting hole portion 65a penetrates the cylindrical portion 35 in the thickness direction of the cylindrical portion 35, and communicates with the suspension-side adjustment length groove portion. For example, the cylinder-side adjusting hole portion 65a is disposed on the right side of the cylindrical portion 35 in a direction about the axis of the cylindrical portion 35.

For example, the suspension-side adjustment length groove portion penetrates the suspension portion 53 in the thickness direction of the suspension portion 53, and is disposed on the right side of the suspension portion 53 in a direction about the axis of the suspension portion 53.

The rack portion is disposed on the lower side of the suspension portion 53 in the direction about the axis of the suspension portion 53. The rack portion is fixed to the suspension portion 53. In the rack portion, the projection portions and recess portions are alternately disposed in the axial direction of the suspension portion 53. The rack portion may be integral with, or separate from, the suspension portion 53.

The adjusting member 65d includes a pinion portion (not shown) which is disposed at a distal end portion of the adjusting member 65d, is provided within the suspension portion 53, and includes a gear which meshes with the rack portion. By the adjusting member 65d rotating about the axis thereof, the pinion portion rotates about the axis of the adjusting member 65d. Then, the pinion portion meshes with the rack portion, and pushes out the rack portion toward the lower side portion 30a, or pushes the rack portion back to the support unit 100 side. Thereby, the suspension portion 53, on which the rack portion is disposed, slides within the cylindrical portion 35 along the axial direction of the suspension portion 53. Thus, in the holding portion 51 which is suspended by the suspension portion 53, the position of insertion of the second dilation-keeping member 403, which is held by the holding portion 51, into the opening part 301 is adjusted.

[Position-Fixing Mechanism 67]

The position-fixing mechanism 67, as illustrated in FIG. 1A, FIG. 1C and FIG. 1D, includes a cylinder-side fixation length groove portion 67a which is provided in the peripheral surface of the cylindrical portion 35 along the axial direction of the cylindrical portion 35; and a suspension-side fixation length groove portion 67b which overlaps the cylinder-side fixation length groove portion 67a and is provided in the peripheral surface of the suspension portion 53 along the axial direction of the suspension portion 53. The position-fixing mechanism 67 further includes a fixing member 67c which is inserted through the upper side portion 30d and cylinder-side fixation length groove portion 67a, and is engaged in the suspension-side fixation length groove portion 67b.

For example, the cylinder-side fixation length groove portion 67a penetrates the cylindrical portion 35 in the thickness direction of the cylindrical portion 35, is disposed on the upper side of the cylindrical portion 35 in the direction about the axis of the cylindrical portion 35, and is disposed with a displacement of 90° relative to the cylinder-side adjusting hole portion 65a.

For example, the suspension-side fixation length groove portion 67b is recessed in the suspension portion 53 in the thickness direction of the suspension portion 53, is disposed on the upper side of the suspension portion 53 in the direction about the axis of the suspension portion 53, and is disposed with a displacement of 90° relative to the suspension-side adjustment length groove portion.

The fixing member 67c includes, for example, a screw. By the fixing member 67c rotating about the axis of the fixing member 67c, the fixing member 67c is engaged with the suspension-side fixation length groove portion 67b, and the suspension portion 53 including the suspension-side adjustment length groove portion is positioned and fixed to the cylindrical portion 35 in the axial direction of the suspension portion 53. Thereby, in the holding portion 51 which is suspended by the suspension portion 53, the position of insertion of the second dilation-keeping member 403, which is held by the holding portion 51, into the opening part 301 is set and fixed.

[Support Unit 100]

As illustrated in FIG. 1B and FIG. 1D, the support unit 100 includes an annular support body portion 101 which is placed on the chest region of the subject 300 (patient), and a rod-shaped support column portion 103 configured to extend from the support body portion 101. The support unit 100 includes a coupling portion 107 which couples a proximal end portion of the cylindrical portion 35 and the support column portion 103, and an angle-adjusting portion 109 which adjusts the angle of the support column portion 103 relative to the coupling portion 107.

The coupling portion 107 functions as an adapter. The coupling portion 107 is detachably fitted in the cylindrical portion 35.

The angle-adjusting portion 109 is attached to the support column portion 103. The angle-adjusting portion 109 is fitted in the coupling portion 107, and the angle-adjusting portion 109 is detachably attached to the coupling portion 107. The angle-adjusting portion 109 functions as an angle-adjusting screw.

[Auxiliary Member 200]

As illustrated in FIG. 1A, FIG. 1C, FIG. 1D and FIG. 2A, the medical dilator 10 further includes an auxiliary member 200 which is disposed in the keeper section 20 and assists a treatment operation of the treatment instrument 500 that treats the opening part 301 and a lumen communicating with the opening part 301. The auxiliary member 200 includes an insertion section 210 which is insertable in the opening part 301. The auxiliary member 200 includes a support section 220 which is disposed on the insertion section 210, thereby being inserted, together with the insertion section 210, into the opening part 301, and is disposed to cross the direction of insertion of the treatment instrument 500 into the opening part 301. The support section 220 supports, for example, a distal end portion of the treatment instrument 500 that is inserted in the opening part 301.

In the present embodiment, the "auxiliary" of the auxiliary member 200 for the treatment operation of the treatment instrument 500 means to assist the approach of the treatment instrument 500 to an affected part. For example, as illustrated in FIG. 4A and FIG. 4B, when the treatment instrument 500 is supported on the support section 220, a support part that is supported by the support section 220 is formed in the treatment instrument 500. By using this support part as a fulcrum 501 of the treatment instrument 500, the treatment instrument 500 further moves toward the affected part, and can reach the vicinity of the affected part including a region in front of the affected part. The "auxiliary" means to assist the treatment operation of the treatment instrument 500, with the fulcrum 501 preventing a displacement of the treatment instrument 500 relative to the affected part, when the treatment instrument 500 treats the affected part.

Figure 2C:
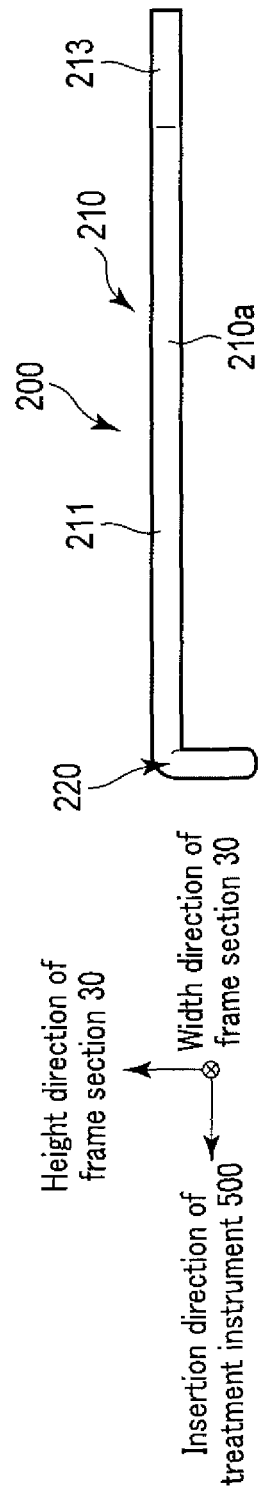
FIG. 2C is a side view of the auxiliary member.

As illustrated in FIG. 2A, the auxiliary member 200 is formed by bending a single line-shaped member. The auxiliary member 200 has, for example, a uniform thinness. As illustrated in FIG. 2B, when the auxiliary member 200 is viewed from above, the auxiliary member 200 is formed, for example, as a substantially bracket ( ⊐ )-shaped frame section. As illustrated in FIG. 2C, when the auxiliary member 200 is viewed from a lateral side, the auxiliary member 200 is formed, for example, as a substantially L-shaped frame section 30. As illustrated in FIGS. 2A and 2B, the auxiliary member 200 is symmetric in the left-and-right direction.

The auxiliary member 200 has such rigidity that, when the treatment instrument 500 is pushed on a support surface 221 (to be described later) of the support section 220, the auxiliary member 200 is not bent by the pushing of the treatment instrument 500, and that the auxiliary member 200 supports the treatment instrument 500 without being bent by the pushing of the treatment instrument 500. In this manner, the auxiliary member 200 has such rigidity that, when the auxiliary member 200 assists the treatment operation of the treatment instrument 500, the auxiliary member 200 is not bent by the pushing, regardless of the treatment, and keeps the preformed shape.

If the above can be achieved, the auxiliary member 200 has such rigidity so that the auxiliary member 200 can be bent in a desired shape in accordance with the treatment instrument 500, a therapy technique, the position of an affected part and the subject 300 by an external force which is stronger than the pushing force of the treatment instrument 500, before the treatment instrument 500 is pushed on the auxiliary member 200, and so that the auxiliary member 200 can keep the bent shape when the treatment instrument 500 has been pushed on the auxiliary member 200 and after the treatment instrument 500 was pushed on the auxiliary member 200.

In this manner, the auxiliary member 200 has such rigidity so that the auxiliary member 200 deforms in a desired shape when the external force which is stronger than the pushing force of the treatment instrument 500 acted on the auxiliary member 200, before the treatment instrument 500 is pushed on the auxiliary member 200, so that the auxiliary member 200 keeps the shape thereof when the pushing force of the treatment instrument 500 and a force weaker than the pushing force act on the auxiliary member 200, and so that the auxiliary member 200 keeps the shape thereof when no external force acts on the auxiliary member 200. That the auxiliary member 200 keeps the shape thereof when no external force acts on the auxiliary member 200 means, for example, a situation in which the auxiliary member 200 is not used for the treatment instrument 500, and the auxiliary member 200 does not bend due to, for example, its own weight or gravitational force. In this manner, the auxiliary member may be variable.

[Insertion Section 210]

As illustrated in FIG. 1A, FIG. 1C, FIG. 1D, FIG. 2A, FIG. 2B and FIG. 2C, the insertion section 210 includes a pair of rod-shaped arm portions 210a which extend in the direction of insertion. The direction of insertion is indicative of a direction perpendicular to the height direction and width direction of the frame section 30, and is indicative of a direction in which the insertion section 210 passes through the opening of the frame section 30. As illustrated in FIG. 2B, the paired arm portions 210a are juxtaposed and spaced apart in the width direction of the frame section 30. As illustrated in FIG. 2C, the arm portion 210a is not bent and is disposed in a straight shape in the height direction of the frame section 30. The arm portions 210a have the same length.

As illustrated in FIG. 1A, FIG. 1C, FIG. 1D, FIG. 2A, FIG. 2B and FIG. 2C, each of the paired arm portions 210a includes an insertion part 211 which is inserted in the opening part 301, and a positioning/fixing part 213 which is disposed in an outside of the opening part 301 and is positioned and fixed relative to the frame section 30 of the keeper section 20 by a positioning/fixing member 250 (to be described later). The insertion part 211 is continuous with the positioning/fixing part 213, and is disposed in front of the positioning/fixing part 213 in the direction of insertion. The phrase "in front of" indicates a side in the insertion direction of the insertion/removal directions.

As illustrated in FIG. 1A, FIG. 1C, FIG. 1D, FIG. 2A, FIG. 2B and FIG. 2C, in the present embodiment, for example, the insertion part 211 includes a distal end portion of the arm portion 210a, and an intermediate portion between the distal end portion and a proximal end portion of the arm portion 210a. In the present embodiment, for example, the positioning/fixing part 213 includes the proximal end portion of the arm portion 210a.

In the meantime, the amount of insertion of the insertion part 211 varies in accordance with the treatment instrument 500 to be used, a therapy technique, the position of an affected part, and the subject 300, and the position of the positioning/fixing part 213 in the frame section 30 varies in accordance with the amount of insertion of the insertion part 211. In accordance with this, a part, which the insertion part 111 includes, and a part, which the positioning/fixing part 213 includes, may differ in accordance with the treatment instrument 500 to be used, a therapy technique, the position of an affected part, and the subject 300. For example, when the amount of insertion is large, the insertion part 211 includes the distal end portion and the intermediate portion, and the positioning/fixing part 213 includes the proximal end portion. For example, when the amount of insertion is small, the insertion part 211 includes the distal end portion, and the positioning/fixing part 213 includes the intermediate portion and the proximal end portion.

As illustrated in FIG. 2B, when the auxiliary member 200 is viewed from above, each of the insertion parts 211 is bent toward the inside of the auxiliary member 200, relative to the proximal end portion of the arm portion 210a. Thus, when the auxiliary member 200 is viewed from above, the insertion parts 211 approach each other in the width direction of the frame section 30, toward the distal end portions (insertion direction). In addition, in the width direction of the frame section 30, the distance between the proximal end portion of one insertion part 211 and the proximal end portion of the other insertion part 211 is greater than the distance between the distal end portion of the one insertion part 211 and the distal end portion of the other insertion part 211. Thus, the auxiliary member 200 is tapered in the direction of insertion.

The positioning/fixing parts 213 are detachably attached to the frame section 30 of the keeper section 20.

[Support Section 220]

As illustrated in FIG. 1A, FIG. 1C, FIG. 1D, FIG. 2A, FIG. 2B, FIG. 2C, FIG. 4A and FIG. 4B, the support section 220 includes the support surface 221 which supports the treatment instrument 500, for example, by the distal end portion of the treatment instrument 500, which is inserted in the opening part 301, being placed on the support surface 221. As illustrated in FIG. 4A and FIG. 4B, the support surface 221 supports the treatment instrument 500 such that the treatment instrument 500, which is placed on the support surface 221, can incline about a fulcrum 501 relative to the direction of insertion. The fulcrum 501 refers to a part of the treatment instrument 500, which is supported on the support surface 221. As illustrated in FIG. 4A, the "incline" means, for example, that the treatment instrument 500 rotates about the fulcrum 501 in a direction about the height direction of the frame section 30. In addition, as illustrated in FIG. 4B, the "incline" means, for example, that the treatment instrument 500 rotates about the fulcrum 501 in a direction about the width direction of the frame section 30. In this manner, the support surface 221 supports the treatment instrument 500 such that the treatment instrument 500 can incline in the up-and-down direction and in the left-and-right direction about the fulcrum 501, relative to the support section 220. The "up-and-down direction" refers to the height direction of the frame section 30, and the "left-and-right direction" refers to the width direction of the frame section 30. As illustrated in FIG. 4A, the support surface 221 supports the treatment instrument 500 such that the treatment instrument 500, which is placed on the support surface 221, can slide on the support surface 221 in the axial direction of the treatment instrument 500 and in the width direction of the frame section 30, which is an orthogonal direction perpendicular to the axial direction of the treatment instrument 500. In the above-mentioned "support", the treatment instrument 500 can be pushed on the support surface 221.

Figure 2D:
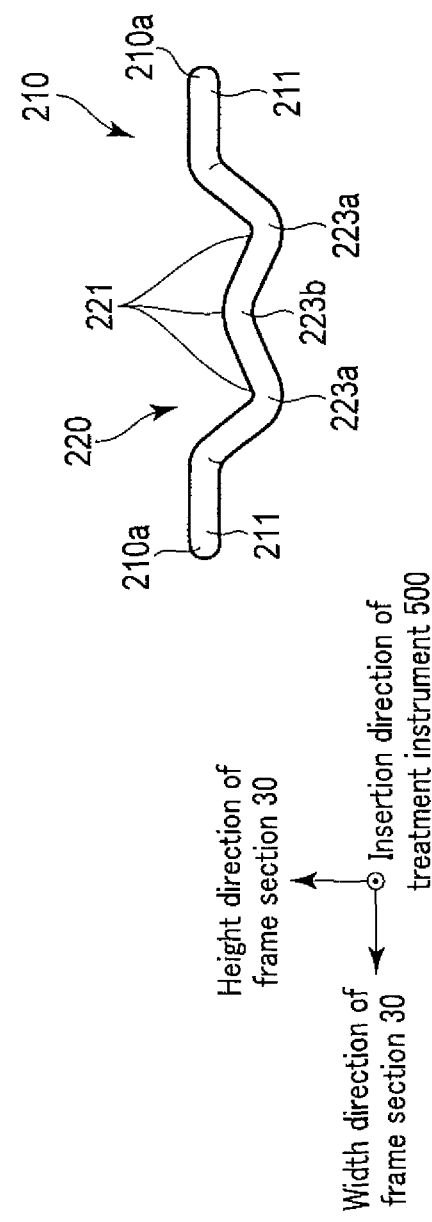
FIG. 2D illustrates an example of a support section, FIG. 2D being is a front view of the support section.

As illustrated in FIG. 2D, this support section 220 has, for example, a wavy shape. Specifically, the support section 220 includes, for example, a pair of recess portions 223a which are recessed in the insertion section 210, and a projection portion 223b which is disposed between one of recess portions 223a and another of the recess portions 223a in the width direction of the frame section 30 and is continuous with the one of recess portions 223a and the another of the recess portions 223a. The recess portion 223a neighbors the projection portion 223b. In this case, the support surface 221 is provided on an inner peripheral surface of the recess portion 223a and on an outer peripheral surface of the projection portion 223b, which is continuous with the inner peripheral surface. In this case, the width of the support surface 221, which is provided on the inner peripheral surface of the recess portion 223a, is substantially equal to the diameter of the treatment instrument 500. The inner peripheral surface of the recess portion 223a and the outer peripheral surface of the projection portion 223b function as the top surface of the support surface 221.

In addition, as illustrated in FIG. 1A, FIG. 1C, FIG. 4A and FIG. 43, the treatment instrument 500 can be placed on the recess portion 223a. An inside diameter of the recess portion 223a is substantially equal to an outside diameter of the treatment instrument 500, and the inner shape of the recess portion 223a is similar to the outer shape of the treatment instrument 500. The inner peripheral surface of the recess portion 223a, on which the treatment instrument 500 is placed, is a curved surface. The inner peripheral surface of the recess portion 223a and the outer peripheral surface of the projection portion 223b are smooth. The outer peripheral surface of the projection portion 223b includes an apex of the projection portion 223b. The apex of the projection portion 223b is disposed at the same position as the insertion part 211 or at a position lower than the insertion part 211 in the height direction of the frame section 30.

As illustrated in FIG. 2C and FIG. 2D, this support section 220 is recessed, relative to the insertion part 211, in the height direction of the frame section 30. Specifically, in the height direction of the frame section 30, the height of the recess portion 223a is substantially equal to the diameter of the treatment instrument 500, or greater than the diameter of the treatment instrument 500, and the apex of the projection portion 223b is lower than both end portions in the width direction of the support section 220. No stepped portion is formed between the recess portion 223a and both end portions, and the support section 220 is gently inclined from both end portions toward the recess portion 223a.

In the meantime, as illustrated in FIG. 2E, the width of the support surface 221, which is provided on the inner peripheral surface of the recess portion 223a, may be greater than the diameter of the treatment instrument 500. The recess portion 223a is planar.

As illustrated in FIG. 2F, the support section 220 may include only a recess portion 223a which is recessed in the insertion section 210. In this case, the support surface 221 is provided on the inner peripheral surface of the recess portion 223a. In this case, the width of the support surface 221 is greater than the diameter of the treatment instrument 500. The recess portion 223a is planar.

Incidentally, if at least one recess portion 223a is provided, the number of recess portions 223a, the number of projection portions 223b, the size of the recess portion 223a and the size of the projection portion 223b do not need to be particularly restricted, and are set in accordance with the treatment instrument 500 to be used, a therapy technique, the position of an affected part, and the subject 300.

As illustrated in FIG. 2A and FIG. 2B, the support section 220 is provided on the insertion section 210 of the auxiliary member 200. Specifically, in the present embodiment, for example, the support section 220 is disposed at a distal end of the insertion part 211 that is the distal end of the auxiliary member 200 and the distal end of the insertion section 210, so as to cross the axial direction of the insertion part 211. As regards "cross" in this context, it is preferable, for example, that the support section 220 is substantially perpendicular to the insertion direction of the treatment instrument 500. It is preferable that the angle formed between the insertion direction and the axial direction of the support section 220 (corresponding to the width direction of the frame section 30) is close to 90°.

As illustrated in FIG. 2A and FIG. 2B, the support section 220 includes one end portion which is continuous with the distal end of one insertion part 211, and the other end portion which is continuous with the distal end of the other insertion part 211. The support section 220 is integral with the two insertion parts 211, and functions as a coupling part which couples the insertion parts 211. At the distal end of the insertion part 211 and the one end portion of the support section 220, which are continuous with each other, and at the distal end of the insertion part 211 and the other end portion of the support section 220, which are continuous with each other, the continuous portions are smoothly bent. The support section 220 is disposed, for example, substantially along the width direction of the frame section 30. In addition, the support section 220 is disposed at the center of the auxiliary member 200 in the width direction of the auxiliary member 200.

[Positioning/Fixing Member 250]

As illustrated in FIG. 1A, FIG. 1C, FIG. 1D, FIG. 3A and FIG. 3B, the medical dilator 10 further includes two positioning/fixing members 250 which position and fix, relative to the frame section 30 of the keeper section 20, the positioning/fixing parts 213 of the two arm portions 210a provided on the auxiliary member 200. The positioning/fixing members 250 attach the insertion section 210 to the frame section 30 and position and fix the insertion section 210 relative to the frame section 30, such that the arm portions 210a are juxtaposed in the width direction of the frame section 30 and the insertion section 210 is inserted in the opening part 301. The respective positioning/fixing members 250 can detachably attach the positioning/fixing parts 213 to the frame section 30.

The two positioning/fixing members 250 are disposed as illustrated in FIG. 1A, FIG. 1C and FIG. 1D. The positioning/fixing members 250 are separate bodies. One positioning/fixing member 250 attaches one arm portion 210a to the right side portion 30b, and positions and fixes the one arm portion 210a relative to the right side portion 30b. The other positioning/fixing member 250 attaches the other arm portion 210a to the left side portion 30c, and positions and fixes the other arm portion 210a relative to the left side portion 30c. In addition, the two positioning/fixing members 250 attach the insertion section 210 to the right side portion 30b and left side portion 30c which are located between the positioning/fixing sections 40 and the lower side portion 30a in the height direction of the frame section 30, and position and fix the insertion section 210 relative to the right side portion 30b and left side portion 30c. The respective positioning/fixing members 250 position and fix the arm portions to the frame section 30 in the state in which the arm portions 210a are positioned and fixed at the same height position.

In the meantime, the position of attachment of the positioning/fixing member 250 to the frame section 30 varies in accordance with the treatment instrument 500 to be used, a therapy technique, the position of an affected part, and the subject 300. Thus, the positioning/fixing members 250 attach the insertion section 210 to the frame section 30, and position and fix the insertion section 210 relative to the frame section 30, in the state in which the support section 220 is disposed in the vicinity of an affected part including a region in front of the affected part.

Although details will be described later, the positioning/fixing member 250 is a separate body from the insertion section 210 and frame section 30, and is replaceable in relation to the insertion section 210 and frame section 30.

The positioning/fixing member 250, which is attached to the left side portion 30c, has the same configuration as the positioning/fixing member 250, which is attached to the right side portion 30b. Thus, in the description below, the positioning/fixing member 250, which is attached to the left side portion 30c, will be described by way of example.

As illustrated in FIG. 3A and FIG. 3B, the positioning/fixing member 250 includes a body portion 251 including a groove-for-frame portion 251a in/from which the left side portion 30c is inserted/removed, and a hole-for-auxiliary portion 251b in/from which the positioning/fixing part 213 of the insertion section 210 is inserted/removed. The positioning/fixing member 250 includes a fixation-for-frame member 253 which pushes the left side portion 30c, which is inserted in the groove-for-frame portion 251a, upon the body portion 251, thereby positioning/fixing the left side portion 30c to the body portion 251; and a fixation-for-auxiliary member 255 which pushes the positioning/fixing part 213, which is inserted in the hole-for-auxiliary portion 251b, upon the body portion 251, thereby positioning/fixing the positioning/fixing part 213 to the body portion 251.

As illustrated in FIG. 3A and FIG. 3B, the groove-for-frame portion 251a is provided along the height direction of the frame section 30. The groove-for-frame portion 251a is formed such that the body portion 251 can slide on the left side portion 30c along the height direction of the frame section 30 via the groove-for-frame portion 251a. The groove-for-frame portion 251a has a recessed shape, the size of the groove-for-frame portion 251a is substantially equal to the size of the left side portion 30c, and the inner shape of the groove-for-frame portion 251a is substantially identical to the outer shape of the left side portion 30c.

As illustrated in FIG. 3A and FIG. 3B, the hole-for-auxiliary portion 251b is provided along the direction of insertion of the treatment instrument 500 (auxiliary member 200) into the opening part 301. The hole-for-auxiliary portion 251b is formed such that the body portion 251 can make the positioning/fixing part 213 slidable along the direction of insertion via the hole-for-auxiliary portion 251b. The hole-for-auxiliary portion 251b has a hollow shape, the size of the hole-for-auxiliary portion 251b is substantially equal to the size of the positioning/fixing part 213, and the inner shape of the hole-for-auxiliary portion 251b is substantially identical to the outer shape of the positioning/fixing part 213.

As illustrated in FIG. 3A and FIG. 3B, the hole-for-auxiliary portion 251b is disposed on the inside of the frame section 30, relative to the groove-for-frame portion 251a.

As described above, the positioning/fixing member 250 attaches the insertion section 210 to the frame section 30 and positions and fixes the insertion section 210 relative to the frame section 30, in the state in which the amount of insertion of the insertion section 210 into the opening part 301 is adjusted such that the support section 220 is disposed in the vicinity of an affected part including a region in front of the affected part.

Specifically, as illustrated in FIG. 3A and FIG. 3B, the fixation-for-frame member 253 pushes the left side portion 30c upon the body portion 251 from the outside toward the inside of the frame section 30 in the width direction of the frame section 30, thereby positioning/fixing the left side portion 30c to the body portion 251.

As illustrated in FIG. 3A and FIG. 3B, the fixation-for-auxiliary member 255 pushes the positioning/fixing part 213 upon the body portion 251 from the inside toward the outside of the frame section 30 in the width direction of the frame section 30, thereby positioning/fixing the positioning/fixing part 213 to the body portion 251.

By the above-described positioning and fixing, the positioning/fixing member 250 attaches the insertion section 210 to the frame section 30 and positions and fixes the insertion section 210 relative to the frame section 30.

In the meantime, the body portion 251 is positioned and fixed in the state in which the body portion 251 is inclined in a direction about the width direction of the frame section 30 relative to the left side portion 30c via the groove-for-frame portion 251a. Thereby, the auxiliary member 200 is positioned and fixed in an inclined state relative to the insertion direction.

The positioning/fixing member 250 is replaced in accordance with the treatment instrument 500 to be used, a therapy technique, the position of an affected part, and the subject 300.

The fixation-for-frame member 253 includes, for example, a screw, and the fixation-for-auxiliary member 255 includes, for example, a screw. The fixation-for-frame member 253 is disposed coaxial with the fixation-for-auxiliary member 255.

[Operation]
[Assembly of Medical Dilator 10]

The proximal end portion of the first dilation-keeping member 401 is fitted in the groove portion 41a.

The proximal end portion of the second dilation-keeping member 403 is inserted in the groove portion 51a, and is fixed to the holding portion 51 by the adjustment-side fixing section 61. Thereby, the second dilation-keeping member 403 is attached to the holding portion 51.

The coupling portion 107 is fitted in the cylindrical portion 35 and angle-adjusting portion 109.

The auxiliary member 200 is positioned and fixed to the frame section 30 by the positioning/fixing members 250.

[Mounting of Medical Dilator 10]

The protection portion 31 covers the upper row 303 of teeth, and the upper jaw fixation portion 33 is fixed to the upper jaw 305. The two first dilation-keeping members 401 are disposed on the angles of mouth 307 side, and the second dilation-keeping members 403 are disposed on the lower jaw 309 side. The protection portion 31, first dilation-keeping members 401 and second dilation-keeping members 403 are inserted in the opening part 301.

At the same time, the insertion parts 211 and support section 220 are inserted in the opening part 301, and the support section 220 is disposed in the vicinity of the affected part including the region in front of the affected part.

The angle-adjusting portion 109 adjusts the angle of the support column portion 103 relative to the coupling portion 107. By this adjustment, the support body portion 101 is mounted on the chest region.

[Adjustment and Fixation]

The respective positioning/fixing sections 40 slide on the frame section 30, thereby adjusting the positions of the first dilation-keeping members 401 relative to the angles of mouth 307.

The insertion direction-adjusting section 63 adjusts the direction of insertion of the second dilation-keeping members 403 into the opening part 301, and fixes the direction of insertion.

The position-adjusting mechanism 65 adjusts the position of insertion of the second dilation-keeping member 403 into the opening part 301. By this adjustment, the second dilation-keeping member 403 dilates the opening part 301 while abutting on, for example, the larynx.

The position-fixing mechanism 67 fixes the position of insertion of the second dilation-keeping member 403, which was adjusted by the position-adjusting mechanism 65 in relation to the opening part 301.

If the support section 220 is disposed in the vicinity of the affected part including the region in front of the affected part, the auxiliary member 200 may be positioned and fixed to the frame section 30 once again by the positioning/fixing members 250 in the state in which the amount of insertion of the insertion section 210 into the opening part 301 has been adjusted.

The angle-adjusting portion 109 adjusts the angle of the support column portion 103 relative to the coupling portion 107. By this adjustment, the support body portion 101 is put in close contact with the chest region.

By the above, the medical dilator 10 is attached to the subject 300 in the state in which the medical dilator 10 is fixed to the subject 300. At the same time, the medical dilator 10 dilates the opening part 301 by the first dilation-keeping members 401 and second dilation-keeping member 403, and keeps the dilated state.

[Auxiliary and Effect of Auxiliary]

As illustrated in FIGS. 1A, 1C, 4A and 4B, the treatment instrument 500 is inserted in the opening part 301 which is dilated by the medical dilator 10. The inserted treatment instrument 500 is supported by being placed on the support surface 221 of the support section 220.

Thus, even if the surgeon continues to grasp the treatment instrument 500 during a surgical operation, the load on the arm of the surgeon can be reduced since the treatment instrument 500 is placed on the support surface 221. Thereby, the time for treatment can be shortened.

When the treatment instrument 500 was supported on the support section 220 of the auxiliary member 200, a support portion, which is supported by the support section 220, is formed on the treatment instrument 500, and the support portion functions as the fulcrum 501 of the treatment instrument 500. In addition, as illustrated in FIG. 4A and FIG. 4B, the treatment instrument 500 further moves toward the affected part by utilizing the fulcrum 501, thereby reaching the vicinity of the affected part including the region in front of the affected part. Thus, even if the lumen is narrow, a fine therapy technique is not required for the surgeon. Hence, by the fulcrum 501, the treatment instrument 500 can be made to easily approach the affected part. Thereby, the time for treatment can be shortened.

Since the larynx is narrow, for example, if unintentional hand movement occurs, there is concern that the treatment instrument 500 treats a region other than the affected part. In the present embodiment, even if unintentional hand movement of the surgeon occurs, it is possible to prevent a region other than the affected part from being treated, since the treatment instrument 500 is supported on the support surface 221. By the above, such skill as suppressing unintentional hand movement can be made needless for the surgeon, and a peroral larynx microsurgery can be performed even without high skill for suppressing unintentional hand movement.

When the treatment instrument 500 treats the affected part, a displacement of the treatment instrument 500 from the affected part can be prevented by the fulcrum 501. Thereby, it is possible to prevent a region other than the affected part from being treated.

The support section 220 is disposed in a manner to cross the insertion direction of the treatment instrument 500. Thus, the support section 220 can surely support the treatment instrument 500.

The support section 220 includes the support surface 221. Thus, the support section 220 can come in surface-contact with the treatment instrument 500, and can surely support the treatment instrument 500. In addition, the fulcrum 501 can exactly be formed.

As illustrated in FIG. 4A and FIG. 4B, the support surface 221 supports the treatment instrument 500, such that the treatment instrument 500, which is placed on the support surface 221, can incline relative to the insertion direction about the fulcrum 501. Thus, the treatment instrument 500 can incline relative to the support surface 221 about the fulcrum 501 in the state in which the treatment instrument 500 is supported on the support surface 221, and can treat a wide range of the affected part in the state in which the treatment instrument 500 is supported on the support surface 221. In this manner, unintentional hand movement can be suppressed and the degree of freedom of treatment can be enhanced.

As illustrated in FIG. 4A, the support surface 221 supports the treatment instrument 500, such that the treatment instrument 500, which is placed on the support surface 221, can slide on the support surface 221 in the axial direction of the treatment instrument 500 and in the width direction of the frame section 30. Thus, the treatment instrument 500 can be made to easily approach the affected part, in the state in which the treatment instrument 500 is supported on the support surface 221. The treatment instrument 500 can be guided to the affected part by the support surface 221.

The support section 220 includes the recess portion 223a and projection portion 223b.

By the treatment instrument 500 being inserted in the recess portion 223a, the movement of the treatment instrument 500 due to unintentional hand movement can further be suppressed. In the state in which the movement is suppressed, as illustrated in FIG. 4A and FIG. 4B, the treatment instrument 500 can incline relative to the support surface 221 about the fulcrum 501 in the state in which the treatment instrument 500 is supported on the support surface 221, as stated above, and can treat a wide range of the affected part in the state in which the treatment instrument 500 is supported on the support surface 221. When the width of the support surface 221, which is provided on the inner peripheral surface of the recess portion 223a, is substantially equal to the diameter of the treatment instrument 500, unintentional hand movement can further be suppressed, and the degree of freedom of treatment can be enhanced. When the width of the support surface 221, which is provided on the inner peripheral surface of the recess portion 223a, is greater than the diameter of the treatment instrument 500, the treatment instrument 500 can incline in a wider range.

As illustrated in FIG. 4A, when the treatment instrument 500 is inserted in the recess portion 223a, the treatment instrument 500 can be inserted/removed in/from the recess portion 223a in the axial direction of the treatment instrument 500, such that the treatment instrument 500 slides on the support surface 221 in the axial direction of the treatment instrument 500 in the state in which the treatment instrument 500 is supported on the support surface 221 provided on the inner peripheral surface of the recess portion 223a. Thus, the treatment instrument 500 can be made to more easily approach the affected part, in the state in which the treatment instrument 500 is supported on the support surface 221. The treatment instrument 500 can be guided to the affected part by the recess portion 223a of the support surface 221. In this manner, the recess portion 223a can function as a guide groove for guiding the treatment instrument 500 toward the affected part. When the width of the support surface 221, which is provided on the inner peripheral surface of the recess portion 223a, is substantially equal to the diameter of the treatment instrument 500, the treatment instrument 500 can be made to more easily approach the affected part, with no displacement, in the state in which the treatment instrument 500 is supported on the support surface 221. When the width of the support surface 221, which is provided on the inner peripheral surface of the recess portion 223a, is greater than the diameter of the treatment instrument 500, the treatment instrument 500 can slide, as described above, on the support surface 221 about the fulcrum 501 in the state in which the treatment instrument 500 is supported on the support surface 221, and can treat a wide range of the affected part in the state in which the treatment instrument 500 is supported on the support surface 221. In this manner, the degree of freedom of treatment can be enhanced.

As illustrated in FIG. 4A, the treatment instrument 500 is slidable, in the width direction of the support surface 221, on the support surface 221 in the insides of the paired recess portions 223a. The treatment instrument 500 is slidable on the support surface 221 in the width direction of the support surface 221 from one recess portion 223a toward the other recess portion 223a via the projection portion 223b. In this manner, the treatment instrument 500 is slidable on the support surface 221 about the fulcrum 501 in the state in which the treatment instrument 500 is supported on the support surface 221, and can treat a wide range of the affected part in the state in which the treatment instrument 500 is supported on the support surface 221.

When a plurality of recess portions 223a are provided, one treatment instrument 500 is inserted in one recess portion 223a, and the other treatment instrument 500 is inserted in the other recess portion 223a. Thus, the plural treatment instruments 500 can be assisted by one auxiliary member 200. In this case, the functions of the treatment instruments 500 may be different from each other.

In this case, the surgeon grasps one treatment instrument 500 by the right hand, and grasps the other treatment instrument 500 by the left hand. In this situation, even if the surgeon continues to grasp the two treatment instruments 500 during a surgical operation, the treatment instruments 500 are supported on the support surface 22, and therefore the load acting on both arms of the surgeon can be reduced.

The insertion section 210 includes a pair of rod-shaped arm portions 210a, and both arm portions 210a are juxtaposed and spaced apart from each other. Thus, it is possible to prevent the insertion section 210 from closing the opening part 301, and to secure an insertion area of the treatment instrument 500 in the opening part 301. Since the positioning/fixing parts 213 are disposed the outside of the opening part 301, the auxiliary member 200 can easily be positioned/fixed relative to the frame section 30. In addition, since the positioning/fixing parts 213 are detachably attached to the frame section 30, the auxiliary member 200 can easily be replaced in relation to the frame section 30.

Since the support section 220 is disposed at the distal ends of the insertion parts 211, the support section 220 can be made to approach up to the region in front of the affected part. Hence, the treatment instrument 500 can be made to quickly approach the affected part.

The auxiliary member 200 is formed by bending a single line-shaped member, and the support section 220 is continuous with the two insertion parts 211. Thus, the structure of the auxiliary member 200 can be made simple and inexpensive.

The continuous portions between the insertion parts 211 of the paired arm portions 201a, on one hand, and the support section 220, on the other hand, are smoothly bent. Thus, even if the continuous portions abut on the vicinity of the affected part, it is possible to prevent the continuous portions from injuring the vicinity of the affected part.

The auxiliary member 200 has such rigidity that, when the treatment instrument 500 is pushed on the support surface 221, the auxiliary member 200 is not bent by the pushing of the treatment instrument 500, and that the auxiliary member 200 supports the treatment instrument 500 without being bent by the pushing of the treatment instrument 500. Thus, when the treatment instrument 500 performs treatment, it is possible to prevent the auxiliary member 200 from being suddenly bent, and to prevent the treatment instrument 500 from treating a part other than the affected part due to the bending.

The positioning/fixing members 250 position and fix the positioning/fixing parts 213 relative to the frame section 30. Thereby, the position of the support section 220 relative to the affected part can freely be adjusted.

Specifically, the positioning/fixing members 250 position and fix, by the fixation-for-frame members 253, the positioning/fixing parts 213 relative to the frame section 30 in the height direction of the frame section 30. Thereby, in the height direction of the frame section 30, the position of the support section 220 relative to the affected part can be freely adjusted. In short, the height position of the support section 220 relative to the affected part can be adjusted.

The positioning/fixing members 250 position and fix, by the fixation-for-auxiliary members 255, the positioning/fixing parts 213 relative to the frame section 30 in the axial direction of the insertion section 210. Thereby, in the insertion direction, the position of the support section 220 relative to the affected part can be freely adjusted. In short, the far/near of the support section 220 relative to the affected part can be adjusted.

The auxiliary member 200 is made attachable/detachable to/from the frame section 30 by the positioning/fixing members 250. Thereby, the range of purposes of use can be increased in accordance with the treatment instrument 500 to be used, a therapy technique, the position of an affected part, and the subject 300.

[Reference Example]

Hereinafter, as a reference example, an example of the treatment instrument 500 in the present embodiment is described.

[Treatment Instrument 500]

Figure 5A:
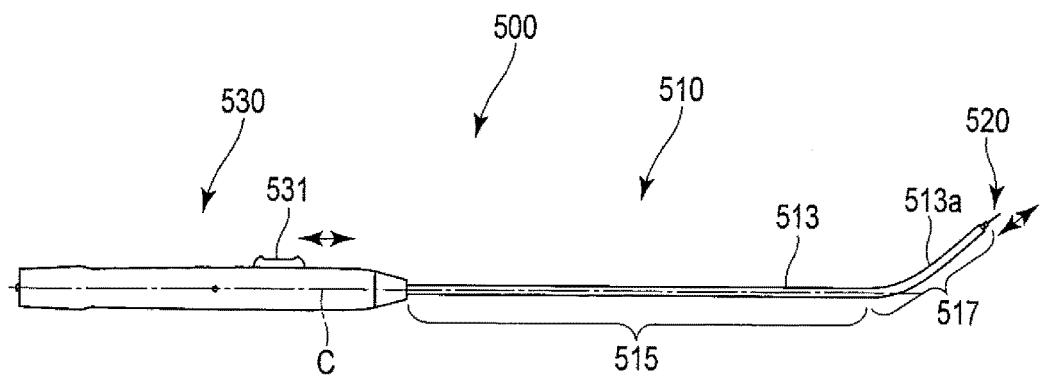
FIG. 5A illustrates a reference example of the treatment instrument, FIG. 5A being a side view of the treatment instrument.

A treatment instrument 500, as illustrated in FIG. 5A, treats an affected part by, for example, energy of high-frequency waves, etc. This treatment includes, for example, cutting. The treatment instrument 500 is, for example, of a pencil type. As illustrated in FIG. 5A, the treatment instrument 500 has a longitudinal axis C. The treatment instrument 500 extends in a direction along the longitudinal axis C, and includes an insertion section 510 which is inserted into the oral cavity and into a lumen via the oral cavity, and a treatment member 520 which is inserted in the insertion section 510 and treats the affected part by the energy which is supplied from an energy supply unit (not shown). The treatment instrument 500 further includes an operation section 530 which is disposed at a proximal end portion of the insertion section 510 and operates the insertion section 510 and treatment member 520.

[Insertion Section 510]

Figure 5B:
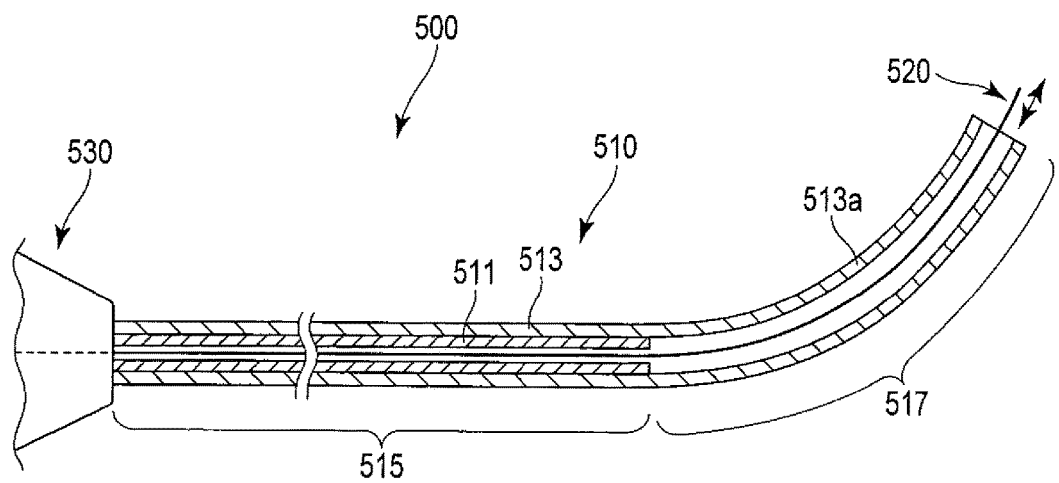
FIG. 5B is a view illustrating the configuration of an insertion section of the treatment instrument illustrated in FIG. 5A.

As illustrated in FIG. 5B, the insertion section 510 includes a rigid cylinder member 511, and a soft cylinder member 513 covering the rigid cylinder member 511. A proximal end portion of the rigid cylinder member 511 and a proximal end portion of the soft cylinder member 513 are coupled to the operation section 530.

As illustrated in FIG. 5B, the rigid cylinder member 511 is inserted in the soft cylinder member 513 in the state in which an outer peripheral surface of the rigid cylinder member 511 is in contact with an inner peripheral surface of the soft cylinder member 513. In the meantime, the rigid cylinder member 511 may cover the soft cylinder member 513. In this case, the soft cylinder member 513 is inserted in the rigid cylinder member 511 in the state in which an outer peripheral surface of the soft cylinder member 513 is in contact with an inner peripheral surface of the rigid cylinder member 511.

The rigid cylinder member 511 is formed of a rigid member of, for example, a metal. This metal is, for instance, stainless steel. As illustrated in FIG. 5B, the rigid cylinder member 511 is shorter than the soft cylinder member 513, and a distal end portion of the rigid cylinder member 511 is disposed inside the soft cylinder member 513. The rigid cylinder member 511 is formed in a straight shape.

As illustrated in FIG. 5B, the soft cylinder member 513 is formed such that the soft cylinder member 513 can be freely bent by the hand of the surgeon and the bent state can be kept. That the bent state is kept means that the soft cylinder member 513 has such desired rigidity that, for example, when the already bent soft cylinder member 513 is abutted on the inner peripheral surface of a lumen, the soft cylinder member 513 can keep the bent state without being further bent by the abutment. Specifically, the soft cylinder member 513 has such rigidity that the soft cylinder member 513 keeps the bent state before treatment, and the soft rigid member 513 is prevented from being further bent unintentionally during the treatment. Such a soft cylinder member 513 is formed by annealing a rigid member of, for example, a metal. This metal is, for instance, stainless steel. Thereby, the soft cylinder member 513 is formed softer than, for example, the rigid cylinder member 511.

As illustrated in FIG. 5A and FIG. 5B, in the rigid cylinder member 511 and soft cylinder member 513 which are disposed and formed as described above, the soft cylinder member 513 includes an extension part 513a which extends more on the front side than the distal end portion of the rigid cylinder member 511. Specifically, since the soft cylinder member 513 is longer than the rigid cylinder member 511, and the rigid cylinder member 511 is not disposed inside the extension part 513a, the extension part 513a, which is formed as a part of the soft cylinder member 513, is freely bent by the hand of the surgeon, as described above, and the bent state is kept. The curvature of bending and the shape of the extension part 513a are freely adjustable in accordance with therapy techniques. The length of this extension part 513a is desirably adjusted in accordance with therapy techniques. The extension part 513a is disposed at least at a distal end portion of the insertion section 510.

As illustrated in FIG. 5B, that part of the insertion section 510, where the rigid cylinder member 511 is disposed, is formed as a double-cylinder part by the rigid cylinder member 511 and a portion of the soft cylinder member 513. This part is not bent by the rigid cylinder member 511 and is disposed in a straight shape by the rigid cylinder member 511. The strength of this part is secured by the rigid cylinder member 511. The length of this part (rigid cylinder member 511) is desirably adjusted in accordance with therapy techniques. This part is disposed at least at a proximal end portion of the insertion section 510.

In this manner, as illustrated in FIG. 5A and FIG. 5B, the insertion section 510 includes a straight portion 515 which includes the rigid cylinder member 511 and a portion of the soft cylinder member 513 and is formed in the straight shape by the rigid cylinder member 511; and a bendable portion 517 which includes the extension part 513a that is the other portion of the soft cylinder member 513, and can bend and keep the bent state by the soft cylinder member 513.

[Treatment Member 520]

As illustrated in FIG. 5B, the treatment member 520 is formed of, for example, a thin line-shaped member. A proximal end portion of the treatment member 520 is coupled to the operation section 530. The treatment member 520 is electrically connected to the energy supply unit. For example, by a footswitch (not shown) being operated, the energy is supplied to the treatment member 520 from the energy supply unit (not shown), and the supply of the energy is stopped.

As illustrated in FIG. 5B, when the rigid cylinder member 511 is inserted in the soft cylinder member 513, the treatment member 520 is inserted in the rigid cylinder member 511 and the extension part 513a. When the soft cylinder member 513 is inserted in the rigid cylinder member 511, the treatment member 520 is inserted in the soft cylinder member 513 including the extension part 513a. In this manner, the treatment member 520 is inserted in the rigid cylinder member 511 or soft cylinder member 513, which is disposed on the inner side, and in the extension part 513a. The treatment member 520 is not in contact with the rigid cylinder member 511 or soft cylinder member 513. In this manner, the treatment member 520 is protected by the insertion section 510 which functions as a sheath.

As illustrated in FIG. 5A, the treatment member 520 is configured to be advanceable/retractable relative to the insertion section 510. Thereby, when the treatment member 520 treats the affected part, the distal end portion of the treatment member 520 projects out of the distal end portion of the insertion section 510 (extension part 513a). When the treatment member 520 finished the treatment, the projecting distal end portion of the treatment member 520 is retracted in the distal end portion of the insertion section 510 (extension part 513a). The advancing/retracting movement of the treatment member 520 is controlled in interlock with the advancing/retracting movement of a switch unit 531 provided on the operation section 530. In this manner, the advancement/retraction of the treatment member 520 from/in the insertion section 510 is switched by the switch unit 531. The amount of projection and the position of retraction are desirably adjusted in accordance with therapy techniques. The amount of projection is less than the length of the insertion section 510. For example, the treatment member 520 is formed longer than the insertion section 510.

As illustrated in FIG. 5A and FIG. 5B, the treatment member 520 is formed such that the treatment member 520 can be bent in accordance with the bending of the extension part 513a and the bent state can be kept. Even in the state in which the extension part 513a is bent, the treatment member 520 is advanceable/retractable relative to the insertion section 510.

[Operation Section 530]

The operation section 530, as illustrated in FIG. 5B, is grasped by the surgeon. The switch unit 531 is disposed at such a position that the surgeon can operate the switch unit 531 by the index finger, when the surgeon holds the operation section 530 in such a manner as to hold a pencil. Thus, the switch unit 531 is disposed, for example, on an outer peripheral surface of a distal end portion of the operation section 530.

The present invention is not limited directly to the above-described embodiments. At the stage of practicing the invention, the structural elements may be modified and embodied without departing from the spirit of the invention. Various inventions may be made by suitably combining a plurality of structural elements disclosed in the embodiments.

What is claimed is:

1. A medical dilator comprising:
   a keeper section inserted in an opening part of a subject, and configured to dilate the opening part and to keep a dilated state of the opening part; and
   an auxiliary member including an insertion section configured to be insertable in the opening part and a support section which is disposed on the insertion section, thereby being inserted into the opening part together with the insertion section, and disposed to cross a direction of insertion of a treatment instrument into the opening part, the support section being configured to support the treatment instrument which is inserted in the opening part, disposed in the keeper section, and configured to assist a treatment operation of the treatment instrument which is configured to treat the opening part and a lumen communicating with the opening part, wherein
   the insertion section includes a pair of rod-shaped arm portions extending in the direction of insertion,
   the pair of arm portions are juxtaposed in a width direction of the keeper section,
   each of the pair of arm portions includes:
      an insertion part which is inserted in the opening part; and
      a position/fixing part which is disposed in an outside of the opening part and is positioned and fixed relative to the keeper section,
   the support section includes:

a support surface configured to support the treatment instrument, by the treatment instrument, which is inserted in the opening part, being placed on the support surface, a pair of recess portions which are recessed in the insertion section, and a projection portion which is disposed between one of the recess portions and another of the recess portions in a width direction of the support section and is continuous with the one of the recess portions and the another of the recess portions, and the support surface is provided on an inner peripheral surface of one of the recess portions and on an outer peripheral surface of the projection portion, the outer peripheral surface being continuous with the inner peripheral surface.

2. The medical dilator according to claim 1, wherein the support surface is configured to support the treatment instrument, such that the treatment instrument, which is placed on the support surface, is inclinable relative to the direction of insertion.

3. The medical dilator according to claim 2, wherein the support surface is configured to support the treatment instrument, such that the treatment instrument, which is placed on the support surface, is slidable on the support surface in an axial direction of the treatment instrument and in an orthogonal direction perpendicular to the axial direction of the treatment instrument.

4. The medical dilator according to claim 1, wherein a width of the support surface, which is provided on the inner peripheral surface of the one of the recess portions, is substantially equal to a diameter of the treatment instrument, or is greater than the diameter.

5. The medical dilator according to claim 1, wherein the positioning/fixing part is detachably attached to the keeper section.

6. The medical dilator according to claim 5, wherein the support section is disposed at a distal end of the insertion part such that the support section crosses an axial direction of the insertion part.

* * * * *